United States Patent [19]
Lai

[11] Patent Number: 5,178,737
[45] Date of Patent: Jan. 12, 1993

[54] ELECTROPHORETIC RESOLUTION OF SINGLE STRAND DNA BY ASYMMETRIC FIELD INVERSION

[75] Inventor: Eric Lai, Chapel Hill, N.C.

[73] Assignee: The University of North Carolina at Chapel Hill, Chapel Hill, N.C.

[21] Appl. No.: 803,316

[22] Filed: Dec. 4, 1991

[51] Int. Cl.$^5$ .................. G01N 27/26; G01N 27/447; B01D 57/02
[52] U.S. Cl. .............................. 204/182.8; 204/299 R; 204/182.1
[58] Field of Search ............... 204/299 R, 182.8, 182.1

[56] References Cited

U.S. PATENT DOCUMENTS

| | | | |
|---|---|---|---|
| 4,737,251 | 4/1988 | Carle et al. | 204/182.8 |
| 4,740,283 | 4/1988 | Laas et al. | 204/182.8 |
| 4,830,726 | 5/1989 | Stamato et al. | 204/299 R |
| 5,084,157 | 1/1992 | Clar et al. | 204/299 R |

OTHER PUBLICATIONS

Daniels, D. L., et al., "Field Inversion Gel Electrophoresis as Applied to DNA Sequencing," Structure and Methods, vol. 1: Human Genome Initiative & DNA Recombination, Sarma, R. H., et al., eds., Adenine Press, pp. 29-35 (1990).
Lai, E., et al., "Effect of Electric Field Switching on the Electrophoretic Mobility of Single-Stranded DNA Molecules in Polyacrylamide Gels," Electrophoresis 10: 65-67 (1989).
Birren, B. W., et al., "The Basis of High Resolution Separation of Small DNAs by Asymmetric-Voltage Field Inversion Electrophoresis and Its Application to DNA Sequencing Gels," Neucleic Acids Research 18 (6): 1481-1487 (1990).
Ulanovsky, L., et al., "DNA Trapping Electrophoresis," Nature 343: 190-192 (11 Jan. 1990).
Higgins, M. J., et al., "Construction of the Physical Map for Three Loci in Chromosome Band 13q14: Comparison to the Genetic Map," Proc. Natl. Acad. Sci. U.S.A. 87: 3415-3419 (1990).

Turmel, C., et al., "Molecular Detrapping and Band Narrowing With High Frequency Modulation of Pulsed Field Electrophoresis," Nucleic Acids Research 18 (3): 569-575 (1990).
Higgins, M. J., et al., "Detection of Saccharomyces Cerevisiae Chromosome Size Markers Directly on Southern Blots of Pulsed-Field Gels With a Single DNA Hybridization Probe" (abstract only), Nucleic Acids Research 17 (23): 10136 (1989).
Heller, C., et al., "A Systematic Study of Field Inversion Gel Electrophoresis," Nucleic Acids Research 17 (15): 5989-6003 (1989).
Turmel, C., et al., "Resolution of Schizosaccharomyces Pombe Chromosomes by Field Inversion Gel Electrophoresis" (abstract only), Nucleic Acids Research 16 (10): 4727 (1988).
Gardiner, K., et al., "Fractionation of Large Mammalian DNA Restriction Fragments Using Vertical Pulsed-Field Gradient Gel Electrophoresis," Somatic Cell and Molecular Genetics 12 (6): 185-195 (1986).
Gardiner, K., et al., "Transverse Alternating Electrophoresis," Nature 331: 371-372 (28 Jan. 1988).
Turmel, C., et al., "High-Resolution Zero Integrated Field Electrophoresis of DNA," Electrophoresis of (List continued on next page.)

Primary Examiner—John Niebling
Assistant Examiner—John S. Starsiak, Jr.
Attorney, Agent, or Firm—Townsend and Townsend

[57] ABSTRACT

Single stranded DNA fragments in sizes above 300 bases are separated electrophoretically in a field inversion technique in which the voltage of the reverse pulse exceeds that of the forward pulse, the duration of the forward pulse exceeds that of the reverse pulse, and the product of voltage and duration for the forward pulse exceeds that of the reverse pulse. The result is an improvement in resolution over previous field inversion techniques, and the elimination of band inversion.

11 Claims, 1 Drawing Sheet

OTHER PUBLICATIONS

*Large DNA Molecules: Theory and Applications*, Cold Spring Harbor Laboratory Press, pp. 101–131 (1990).

Heiger, D. N., et al., "Separation of DNA Restriction Fragments by High Performance Capillary Electrophoresis With Low and Zero Cross-Linked Polyacrylamide Using Continuous and Pulsed Electric Fields," *Journal of Chromatography* 516: 33–48 (1990).

Cantor, C. R., et al., "Voltage Ramp Pulsed Field Gel Electrophoresis Separation of Large DNA Molecules," *Electrophoresis '86*, Dunn, M. J. (ed), VCH Verlagsgesellschaft, Weinheim (1986).

Jaan Noolandi, "A Possible Application of Zero Integrated Pulsed Field Gel Electrophoresis (ZIFE) to DNA Sequence Analysis" Makromol. Chem. Rapid Commun. 12 (1991) 31–35.

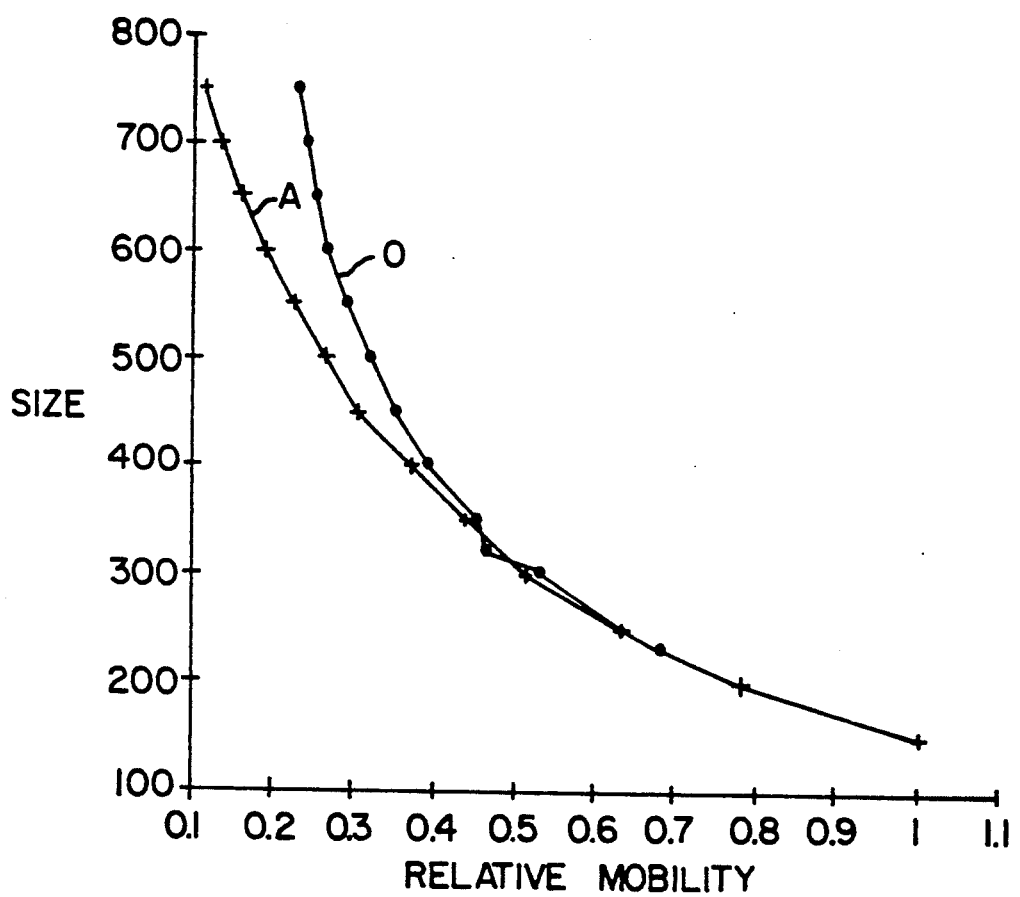

ELECTROPHORETIC RESOLUTION OF SINGLE STRAND DNA BY ASYMMETRIC FIELD INVERSION

This invention lies in the field of electrophoretic separations of single strand DNA, and relates in particular to methods for improving the resolution of single strand DNA molecules.

BACKGROUND OF THE INVENTION

A technique of rapidly growing use in laboratory manipulations of DNA is that of pulsed field electrophoresis. The technique was developed to resolve DNA fragments on the basis of size. In each of its many variations, this technique involves the switching of the electric field back and forth between two or more fields which differ in direction, to cause a periodic reorientation of the DNA strands. The degree of reorientation occurring within each pulse varies with the length of each strand, with the result that the net rate of movement of any particular strand in an overall direction of migration varies with the length of that strand, thereby permitting resolution according to strand length.

Early investigations of the technique include the frequently referenced patent of Cantor, et al., U.S. Pat. No. 4,473,452 (Sep. 25, 1984), and the companion paper, Schwartz, D. C., et al., "New Techniques For Purifying Large DNAs and Studying Their Properties and Packaging," *Cold Spring Harbor Symposia on Quantitative Biology* 47:189–195 (1983). The switching protocol disclosed by Cantor and Schwartz is between two electric fields in directions which are transverse (generally orthogonal) to each other, both in the plane of a slab gel, with intensity and duration differing between the two fields. The angle between the two fields changed as the DNA progressed along the gel, but the result is an overall migration direction which generally follows a line which bisects the angle between the two field directions. Variations of the technique include the use of angles other than 90°, e.g., 120°, and various refinements and adjustments for achieving control over field homogeneity. In a further variation of the technique, the two field directions are transverse to the plane of the gel as well as to each other, with the plane of the gel bisecting the angle between them. This variation is described by Gardiner, K., et al., *Somatic Cell and Molecular Genetics* 12(6): 185–195 (1986) and Gardiner, K., et al., *Nature* 331:371-2 (28 Jan. 1988), and is referred to as "transverse alternating field electrophoresis" (TAFE). Here, the two fields are of the same intensity and switching is done at equal time intervals, but again, the angle between the fields changes as the DNA migrates along the gel.

A second group of pulsed field techniques involve field inversion, or one-dimensional pulsing, rather than orthogonally oriented fields. In this group, known as "field inversion gel electrophoresis" (FIGE), the alternation is between two fields rotated 180° with respect to each other rather than 90°, 120° or any other transverse angle. A description of this technique is offered by Carle, G. F., et al., U.S. Pat. No. 4,737,251 (Apr. 12, 1988). According to the Carle, et al. method, net migration in one direction is achieved by an asymmetric field inversion profile, using either pulses of unequal duration, the forward pulse being longer than the reverse, or pulses of the same duration but unequal voltage gradient, the gradient in the forward direction being greater than that in the reverse.

A problem associated with FIGE techniques is band inversion, in which intermediate-size molecules migrate slower than both smaller and larger ones, the size vs. mobility curve turning back on itself, superimposing small molecules over large by giving both the same mobility. One attempt to overcome this problem is the technique known as "zero integrated field electrophoresis" (ZIFE), and is described by Turmel, C., et al., "High-Resolution Zero Integrated Field Electrophoresis of DNA," *Electrophoresis of Large DNA Molecules: Theory and Applications,* Cold Spring Harbor Laboratory Press, pp. 101-131 (1990). Here, the time-averaged voltage gradient $E_{AV}$ is defined by the following equation:

$$E_{AV} = (E_1 t_1 - E_2 t_2)/(t_1 + t_2)$$

where E denotes the gradient (V/cm) and t the duration (sec), with the subscript 1 referring to the forward direction and 2 the reverse. Although the name given the technique by the authors denotes $E_{AV}$ equal to zero with $E_1 \neq E_2$ the preference of the authors is for $E_{AV}$ "slightly larger than zero," on the order of 0.33. This is said to eliminate band inversion for molecules of larger than 23 kbp in size.

These techniques have been developed for, and used almost entirely in, separations of double stranded DNA. For single stranded DNA, their use has met with limited success. Despite the ability of these techniques to improve the resolution of large double stranded DNA, they appear to offer little improvement for large single stranded DNA, where resolution is particularly difficult, if not lacking entirely, for fragments greater than 400 bases in length. The most widely used field inversion technique for single strand DNA has involved equal voltage gradients forward and reverse, with the forward duration exceeding the reverse. This results in a minor improvement in separating large single stranded DNA. It also results however in band inversion which, as in double stranded DNA separations, can obscure the separation. In addition, the lack of a flexible high voltage switching power supply has limited the investigation of the effects of pulsed field techniques on the separation of single stranded DNA. As a result, pulsed field electrophoresis has not been a viable technique for DNA sequencing or other separations involving single stranded DNA.

While fragments up to about 250 bases in length can be separated by conventional equipment and techniques, a variety of complex and unwieldy methods have been used for longer sequences. These include the use of gels which are longer than the conventional and commercially available sequencing gels (which are 40 cm to 80 cm in length), the use of voltage, buffer and salt gradients to vary the spacing of the bands along the length of the gel (neither of these methods gives a true improvement in resolution), the use of $^{35}S$ isotope, the use of multiple lane sets loaded at different times to vary the duration of each run, the attachment of biotin, streptavidin or other large molecule (as reported by Ulanovsky, L., et al., "DNA trapping electrophoresis," *Nature* 343:190–192, 11 Jan. 1990), and methods by which the separated bands are moved continuously past a fixed detector such as an automated fluorescence detector.

An simple and effective method for separating single strand DNA which is effective over a wide range of strand lengths is needed. The present invention provides such a method and overcomes many of the problems of prior art techniques in a manner which demonstrates unexpected success.

SUMMARY OF THE INVENTION

It has now been discovered that the resolution of single stranded DNA in size ranges which have previously been difficult to resolve is markedly improved by the use of an asymmetric field inversion technique in which the voltage of the reverse pulse exceeds that of the forward pulse, the duration of the forward pulse exceeds that of the reverse pulse, and the product of voltage and duration for the forward pulse exceeds that of the reverse pulse. Expressed mathematically, these relations are as follows:

$$E_r/E_f \geq 2$$

$$t_f/t_r \geq 1.25$$

$$1.1 \leq (E_f t_f)/(E_r t_r) \leq 2.0$$

where $E_f$ and $t_f$ are the voltage gradient and duration, respectively, of the forward pulse and $E_r$ and $t_r$ are the voltage gradient and duration, respectively, of the reverse pulse. Voltage gradients in this specification are expressed as volts per cm, and represent the entire voltage drop across the separation medium divided by the length of the medium. The term "forward" as it is used herein refers to the direction of net migration of the DNA, which in conventionally configured gels occurs from the well to the bottom of the gel.

Optimum voltage gradients and voltage gradient ratios for a particular separation will vary depending on the size of the single stranded DNA which is sought to be separated. In general, the optimum voltage gradient and voltage gradient ratio will increase as the average sequence length increases. All voltage gradients will be high, however, to enable the separations to be completed within reasonable time periods, since separations of this type tend to require considerable lengths of time.

Other features and advantages of the invention will become apparent from the description which follows.

BRIEF DESCRIPTION OF THE FIGURE

The FIGURE is a plot of strand length vs. relative mobility for single strand DNA upon electrophoresis, showing the results obtained using a field inversion technique in accordance with the present invention beside corresponding results obtained without field inversion.

DETAILED DESCRIPTION OF THE INVENTION AND PREFERRED EMBODIMENTS

This invention permits the use of conventional DNA sequencing cells and other electrophoretic separation systems for separating single stranded DNA. The separation media in cells for DNA sequencing are generally gels within the range of about 30 cm to about 100 cm in length, the most common being from about 40 cm to about 80 cm. The separations will generally be performed at voltage gradients of about 10 V/cm or higher in both the forward and reverse segments of each pulse. Preferred voltages will be about 10 V/cm to about 100 V/cm, the most preferred being from about 30 V/cm to about 100 V/cm. The invention extends to systems in which the voltage gradients and durations are constant from one pulse to the next, as well as to those in which either the voltage gradients, durations or both vary from one pulse to the next. A particularly preferred protocol is one in which the pulse duration is ramped, i.e., increases successively.

While the improvement of the present invention is observed with a combination of limitations on these parameters, preferred ranges apply to some of these limitations as well. A preferred range of the voltage gradient ratio $E_r/E_f$, for example, is the range of about 2.0 to about 10, and a more preferred range is about 2.25 to about 5. A preferred range for the ratio of the durations of the forward and reverse segments of the pulses, $t_f/t_r$ is about 2 to about 20, and a more preferred range is about 2.5 to about 5. The duration of each segment may vary considerably, and like the voltage gradient, the optimum will vary with the size range sought to be separated. In most applications, best results will be obtained with forward and reverse durations each greater than or equal to about 0.01 sec, preferably from about 0.03 sec to about 3 sec, and more preferably from about 0.1 sec to about 1 sec. Other preferences are determinable by routine experimentation.

The methods of this invention are not restricted to electrophoretic separation media of any particular configuration or composition. Both gels and viscous solutions such as solutions of linear polyacrylamide may be used. Since the two electric fields are along a common axis, the invention may be used in both slab-shaped media and capillary-retained media. In most applications, however, a slab gel will be used, of a length in accordance with the discussion above.

Excessive heating of the separation medium due to the electric current will be prevented by conventional cooling procedures, which in many cases are built into the support for the medium or into other components of the construction of the electrophoresis cell. A typical DNA sequencing system which is useful in the practice of this invention is the Sequi-Gen ® Nucleic Acid Sequencing System of Bio-Rad Laboratories, Inc., Hercules, Calif., which utilizes a vertical slab gel with lengths ranging from 40 cm to 80 cm.

The electrodes will be driven by a power supply and field switching unit designed for pulsed field electrophoresis. Among the various commercially available units are the Model 3000xi Electrophoresis Power Supply, in combination with a modified Pulsewave 760 Electrophoretic Field Switcher capable of switching 3000 V, all obtainable from Bio-Rad Laboratories, Inc., Hercules, Calif. Alternatively, the electrodes can be driven by a switching power supply such as units obtainable from TRAK, Inc., Tampa, Fla.

The gel and the buffers may both be of any conventional composition known to be useful in electrophoretic separations. Examples of gels are agarose, polyacrylamide and starch gels. The concentration of the gel may also be varied, and will be selected in accordance with conventional practice based on considerations known to the skilled laboratory technician.

Single strand DNA which will benefit from the methods of this invention will be those molecules of about 200 or more bases in length. The benefit is particularly pronounced among molecules of about 300 or more bases in length, and extends to molecules of above 1000 bases.

The length of time required for separation of the DNA molecules using this invention is not critical and may vary widely, depending on the other variables in the system. In most cases, the separation will be complete within about 8 hours to about 16 hours.

Once the separation has been completed, the bands may be detected, identified and quantified by conventional procedures. Examples of suitable detection techniques are radioactivity, fluorescence, and chemiluminescence. The method is adaptable to both manual and automated means of detection.

The following examples are offered for purposes of illustration, and are intended neither to limit nor to define the invention in any manner.

EXAMPLES

A series of electrophoretic separations were run, each using the same mixture of single strand DNA of varying strand length and each using the same gel, the separations varying in the voltage gradient and field switching protocol. The mixture ranged in size from 15 bases to 1000 bases, and the separation medium was a 5% polyacrylamide slab gel measuring 80 cm (length) by 21 cm (width) by 0.04 cm (thickness), mounted in a DNA sequencing electrophoresis cell. All switching was performed with rectangular waveform pulses.

The separations used in this comparison include:
one run performed with a constant unidirectional field of 2800 V (no pulsing)—Run "0"
one run performed in accordance with the protocol described by Turmel, C., et al., "High-Resolution Zero Integrated Field Electrophoresis of DNA," *Electrophoresis of Large DNA Molecules: Theory and Applications*, Cold Spring Harbor Laboratory Press, pp. 101–131 (1990), i.e., $E_r/E_f < 1$, $t_f/t_r < 1$, and $E_f t_f/E_r t_r \geq 1$—Run "i"
one run performed in accordance with a protocol similar to that described by Birren, B. W., et al., "The basis of high resolution separation of small DNAs by asymmetric-voltage field inversion electrophoresis and its application to DNA sequencing gels," *Nucleic Acids Research* 18(6): 1481–1487 (1990)—Run "ii"
two runs performed in accordance with the protocol described by Carle, G. F., et al., U.S. Pat. No. 4,737,251, "Field Inversion Gel Electrophoresis," issued Apr. 12, 1988, i.e., $E_r/E_f = 1$, $t_f/t_r > 1$ —Runs "iii" and "iv"
four runs performed in accordance with other protocols outside this invention—Runs "v" through "viii"
two runs performed in accordance with this invention, i.e., $E_r/E_f \geq 2.0$, $t_f/t_r \geq 1.25$, and $1.1 \leq E_f t_f/E_r t_r \leq 2.0$—Runs "A" and "B"

Results from the separations are shown in the table below, and results from Runs A and 0 are also shown in the FIGURE. In the table, mobilities are expressed in relative terms, all normalized to the mobility of a DNA molecule 150 bases (150b) in length. By comparing the spread in mobility between 300-base and 700-base DNA molecules among the various runs, one can see that the spread obtainable without pulsing is either not improved at all or improved only moderately by pulsing according to any of the protocols outside the invention, whereas significant improvement is achieved by pulsing according to the invention. In the FIGURE, the abscissa represents the mobility of the molecules relative to that of the 50-base molecule, and the ordinate represents the size of the molecules in bases. The curve representing Run A shows the improvement relative to Run 0, and illustrates that the present invention separates molecules differing in size by as little as 50 bases to a degree sufficient to permit differentiation.

Pulsed-Field Electrophoresis of Single Strand DNA in 80 cm Gel:
Mobility vs. Size Under Various Field Switching Protocols

| Run | $E_f$ (V/cm) | $t_f$ (sec) | $E_r$ (V/cm) | $t_r$ (sec) | $E_r/E_f$ | $t_f/t_r$ | $E_f t_f/E_r t_r$ | Mobility Relative to 150 b DNA Size: 300 b | 500 b | 700 b |
|---|---|---|---|---|---|---|---|---|---|---|
| 0 | 35 | (No pulsing) | | | | | | 0.57 | 0.36 | 0.23 |
| | | | Protocols Outside This Invention: | | | | | | | |
| i | 35 | 1 | 12.5 | 2.5 | 0.4 | 0.4 | 1.0 | 0.54 | 0.36 | 0.31 |
| ii | 17.5 | 0.02 | 12.5 | 0.002 | 0.71 | 10 | 14 | 0.52 | 0.29 | |
| iii | 35 | 1 | 35 | 0.25 | 1.0 | 4.0 | 4.0 | 0.54 | 0.34 | 0.26 |
| iv | 35 | 1 | 35 | 0.5 | 1.0 | 2.0 | 2.0 | 0.54 | 0.34 | 0.26 |
| v | 12.5 | 1 | 35 | 0.1 | 2.8 | 10.0 | 3.6 | 0.53 | 0.30 | 0.22 |
| vi | 18.75 | 1 | 35 | 0.4 | 1.9 | 2.5 | 1.3 | 0.54 | 0.34 | 0.24 |
| vii | 25 | 1 | 35 | 0.1 | 1.4 | 10.0 | 7.2 | 0.54 | 0.34 | 0.23 |
| viii | 25 | 1 | 35 | 0.5 | 1.4 | 2.0 | 1.4 | 0.52 | 0.34 | 0.23 |
| | | | This Invention: | | | | | | | |
| A | 12.5 | 1 | 35 | 0.2 | 2.8 | 5.0 | 1.8 | 0.51 | 0.27 | 0.13 |
| B | 12.5 | 1 | 35 | 0.3 | 2.8 | 3.3 | 1.2 | 0.51 | 0.27 | 0.13 |

The foregoing is offered primarily for purposes of illustration. Certain variations, modifications and substitutions in the materials and procedures beyond those disclosed herein will be readily apparent to those skilled in the art, who will recognize that such changes will provide equivalent results and can be made without departing from the spirit and underlying concepts of the invention.

What is claimed is:

1. A method for the electrophoretic separation of a mixture of single strand DNA molecules of 200 or more bases in length along a preselected direction of migration in an electrophoretic separation medium, said method comprising imposing across said medium electrical fields alternating between a forward field and a reverse field whose direction is rotated 180° with respect to said forward field, said forward field being along said direction of migration, said forward and reverse fields having voltage gradients and durations as follows:

$E_f$ and $E_r$ are each greater than or equal to about 10 V/cm;

$E_r/E_f$ is greater than or equal to about 2.0;

$t_f$ and $t_r$ are each greater than or equal to at least about 0.01 sec;

$t_f/t_r$ is greater than or equal to about 1.25; and $E_f t_f/E_r t_r$ is from about 1.1 to about 2.0;

where $E_f$ and $t_f$ are the voltage gradient and duration of said forward field and $E_r$ and $t_r$ are the voltage gradient and duration of said reverse field.

2. A method in accordance with claim 1 in which $E_f$ and $E_r$ are each from about 10 V/cm to about 100 V/cm.

3. A method in accordance with claim 1 in which $E_r/E_f$ is from about 2.0 to about 10.

4. A method in accordance with claim 1 in which $E_f$ and $E_r$ are each from about 30 V/cm to about 100 V/cm, and $E_r/E_f$ is from about 2.25 to about 5.

5. A method in accordance with claim 1 in which $t_f$ and $t_r$ are each from about 0.03 sec to about 3 sec.

6. A method in accordance with claim 1 in which $t_f/t_r$ is from about 2 to about 20.

7. A method in accordance with claim 1 in which $t_f$ and $t_r$ are each from about 0.1 sec to about 1 sec, and $t_f/t_r$ is from about 2.5 to about 5.

8. A method in accordance with claim 1 in which $E_f$ and $E_r$ are each from about 10 V/cm to about 100 V/cm, $E_r/E_f$ is from about 2.0 to about 10, and $t_f/t_r$ is from about 2 to about 20.

9. A method in accordance with claim 1 in which $E_f$ and $E_r$ are each from about 30 V/cm to about 100 V/cm, $E_r/E_f$ is from about 2.25 to about 5, and $t_f/t_r$ is from about 1.5 to about 5.

10. A method for the electrophoretic separation of a mixture of single strand DNA molecules of 300 or more bases in length along a preselected direction of migration in a gel, said method comprising imposing across said gel electrical fields alternating between a forward field and a reverse field whose direction is rotated 180° with respect to said forward field, said forward field being along said direction of migration, said forward and reverse fields having voltage gradients and durations as follows:

$E_f$ and $E_r$ are each from about 10 V/cm to about 100 V/cm;

$E_r/E_f$ is from about 2.0 to about 10;

$t_f/t_r$ is from about 2 to about 20; and $E_f t_f/E_r t_r$ is from about 1.1 to about 2.0;

where $E_f$ and $t_f$ are the voltage gradient and duration of said forward field and $E_r$ and $t_r$ are the voltage gradient and duration of said reverse field.

11. A method for the electrophoretic separation of a mixture of single strand DNA molecules of 300 or more bases in length along a preselected direction of migration in a gel, said method comprising imposing across said gel electrical fields alternating between a forward field and a reverse field whose direction is rotated 180° with respect to said forward field, said forward field being along said direction of migration, said forward and reverse fields having voltage gradients and durations as follows:

$E_f$ and $E_r$ are each from about 30 V/cm to about 100 V/cm;

$E_r/E_f$ is from about 2.25 to about 5;

$t_f/t_r$ is from about 2.5 to about 5; and $E_f t_f/E_r t_r$ is from about 1.1 to about 2.0;

where $E_f$ and $t_f$ are the voltage gradient and duration of said forward field and $E_r$ and $t_r$ are the voltage gradient and duration of said reverse field.

* * * * *